United States Patent [19]
Meyer, Jr. et al.

[11] Patent Number: 5,177,196
[45] Date of Patent: Jan. 5, 1993

[54] OLIGO (α-ARABINOFURANOSYL NUCLEOTIDES) AND α-ARABINOFURANOSYL PRECURSORS THEREOF

[75] Inventors: Rich B. Meyer, Jr., Woodinville; A. David Adams, Snohomish; Charles R. Petrie, Woodinville, all of Wash.

[73] Assignee: Microprobe Corporation, Bothell, Wash.

[21] Appl. No.: 568,391

[22] Filed: Aug. 16, 1990

[51] Int. Cl.$^5$ .............................................. C67H 17/00
[52] U.S. Cl. .................................. 536/22.1; 536/25.5; 536/25.6; 530/387.5
[58] Field of Search ............................... 435/6; 536/27

[56] References Cited

U.S. PATENT DOCUMENTS
4,760,017  7/1988  McCormick ........................... 435/6

FOREIGN PATENT DOCUMENTS
0227459  1/1987  European Pat. Off.

OTHER PUBLICATIONS
Hélène, C., et al., *Pont. Acad. Sci. Scripta Varia* 70:205-222 (year unknown).
Gautier, C., et al., *Nucleic Acids Res.* 15:6625-6641 (1987).
Doan, T. L., et al., *Nucleic Acids Res.* 15:7749-7760.
Praseuth, D., et al., *Biochemistry* 27:3031-3038 (1988).
Knorre, D. G., et al., *Progress in Nucleic Acid Research and Molecular Biology* 32:291-320 (1985).
Praseuth, D., et al., *Proc. Natl. Acad. Sci. U.S.A.* 85:1349-1353.
Morvan, F., et al., *Nucleic Acids Res.* 15:7027-7044 (1987).
Sun, J., et al., *Nucleic Acids Res.* 15:6149-6158 (1987).
Cazenave, C., et al., *Nucleic Acids Res.* 15:10507-10521 (1987).
Gagnor, C., et al., *Nucleic Acids Res.* 15:10419-10436 (1987).
Thuong, N. T., et al., *Proc. Natl. Acad. Sci. USA* 84:5129-5133 (1987).
Lee, W. W. et al., *J. Med. Chem.* 14:819-823 (1971).
Davoll, J., et al., *Science* 74:1563-1566 (1952).

*Primary Examiner*—John W. Rollins
*Attorney, Agent, or Firm*—Susan L. Preston; Debra K. Leith; Gabor L. Szekeres

[57] ABSTRACT

Novel oligonucleotides formed from α-D-arabinofuranosyl nucleoside monomers, including oligonucleotides in which one or more of the monomer units is functionalized, are disclosed herein, as well as functionalized monomeric α-D-arabinofuranosyl nucleosides and nucleotides. A generic formula for the oligomers is:

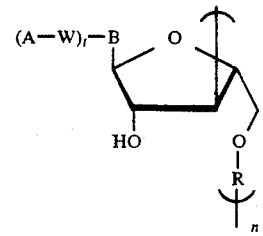

in which B is a nucleotide base which will vary from one monomeric unit to the next in a preselected oligonucleotide sequence; R is phosphate, phsophorothioate, phosphoramidate, or alkanephosphonate; t is 1 for functionalized monomeric units and zero for the others; W is a chemical linker arm; A is a functional group; and n is the number of monomeric units in the oligomer. The oligomers are useful for diagnostic and chemotherapeutic uses. A novel reaction is also disclosed, in which an α-D-arabinofuranosyl nucleoside with exposed hydroxyls at the 2'- and 3'-positions is selectively protected at the 2'-position in a single reaction.

14 Claims, No Drawings

OLIGO (α-ARABINOFURANOSYL NUCLEOTIDES) AND α-ARABINOFURANOSYL PRECURSORS THEREOF

This invention was made with government support under Research Grant CA 40336 awarded by the National Institutes of Health. The government has certain rights in the invention.

FIELD OF THE INVENTION

This invention relates to oligonucleotides comprising α-D-arabinofuranosyl nucleosides, and to the use of these novel compositions for diagnostic and chemotherapeutic purposes.

BACKGROUND ART

Oligonucleotides are useful as diagnostic probes for the detection of "target" DNA or RNA sequences. A probe generally contains a sequence of ribo- or deoxyribonucleic acid complementary to the target sequence and a means for detection. A probe in which the nucleotides of the sequence contain natural β-arabinose rather than ribose, together with a procedure which utilizes an anti-arabinose antibody as the means of detection, is proposed by McCormick, R. M., U.S. Pat. No. 4,760,017, filed Dec. 23, 1985, issued Jul. 26, 1988.

Oligonucleotides may also be used as chemotherapeutic agents to control the expression of gene sequences unique to an invading organism, such as a virus, a fungus or a bacterium. In nature, some RNA expression in bacteria is controlled by "antisense" RNA, which exerts its effect by forming RNA:RNA hybrids with complementary target RNAs and modulating or inactivating their biological activity. A variety of recent studies using plasmid vectors for the introduction of antisense RNAs into eukaryotic cells have shown that they effectively inhibit expression of mRNA targets in vivo; see Green, P. J., et al. *Ann. Rev. Biochem.* 55:569–597 (1986). Additionally, a specific mRNA amongst a large number of mRNAs can be selectively inactivated for protein synthesis by hybridization with a complementary DNA restriction fragment, which binds to the mRNA and prevents its translation into protein on ribosomes. See Paterson, B. M., et al., *Proc. Natl. Acad. Sci.* 74:4370–4374 (1977); and Hastie, N. D., et al., Proc. Natl. Acad. Sci. 75:1217–1221 (1978).

It has been shown that an appropriate small antisense oligonucleotide probe can inhibit replication of Rous Sarcoma Virus (RSV) in cell culture, as reported by Zamecnik, P. C., et al., Proc. Natl. Acad. Sci. USA 75:280 (1978), and that RSV viral RNA translation is inhibited under these conditions, as reported by Stephenson, et al., *Proc. Natl. Acad. Sci. USA* 75:285–288 (1978). It has also been shown that oligonucleotides complementary to a mRNA splice acceptor site in the HIV virus genome (the causative agent of AIDS) are capable of inhibiting expression and replication in cell culture; see Zamecnik, P. C., et al., *Proc. Natl. Acad. Sci. USA* 83:4143 (1986); Goodchild, et al., *Proc. Natl. Acad. Sci USA* 85:5507–5511 (1988).

Uncharged methylphosphonate oligodeoxynucleotides with a sequence complementary to the initiation codon regions of rabbit globin mRNA inhibited the translation of the mRNA in both cell-free systems and in rabbit reticulocytes, as reported by Blake, K. R., et al., *Biochemistry* 24:6139–6145 (1985). Another uncharged methylphosphonate oligonucleotide analog, an 8-nucleotide sequence complementary to the acceptor splice junction of a mRNA of Herpes simplex virus, Type 1, can inhibit virus replication in intact Vero cells. However, fairly high concentrations (>25 μM) of this nonionic probe were required for this inhibition.

In studies of the properties of oligomers composed of the α-deoxy-anomers of the natural β-deoxynucleosides, it has been shown that oligo-(α-thymidylate) binds to polyadenylate much more strongly than the natural β-oligomer, as reported by Thuong, N. T., et al., *Proc. Natl. Acad. Sci. USA* 84:5129–5133 (1987). This α-deoxyoligomer is also highly nuclease resistant, as reported by Cazenave, C., et al., *Nucleic Acids Res.* 15:10507–10521 (1987). Another α-oligomer, α-deoxy-(G$_2$T$_{12}$G$_2$) has been shown to bind to (dA)$_{12}$ with a T$_m$ of 53°, whereas the corresponding oligo-(β-anomer) binds with a T$_m$ of 27°; see Gagnor, C., et al., *Nucleic Acids Res.* 15:10419–10436 (1987). Additionally, the antisense α-oligodeoxynucleotide binds parallel to the sense strand; see Sun, J., et al., *Nucleic Acids Res.* 15:6149–6158 (1987); and Morvan, F., et al., *Nucleic Acids Res.* 15:7027–7044 (1987). However, while α-deoxyribofuranosides provide nuclease resistance and have a greater hybrid stability as compared to the corresponding β-oligomers, they are very difficult to synthesize because the α-anomers of the deoxynucleosides cannot be isolated in nature and are difficult and expensive to prepare synthetically Therefore, the difficulty remained to find oligonucleotides which were easy to synthesize, were nuclease resistant, exhibited hybrid stability, and had improved hybridization efficiency.

SUMMARY OF THE INVENTION

This invention relates to functionalized α-D-arabinofuranosyl nucleosides and nucleotides, to oligonucleotides formed from α-D-arabinofuranosyl nucleoside monomer units, and to oligonucleotides formed from α-D-arabinofuranosyl nucleoside monomer units in which one or more of the units is functionalized, and to the use of these novel compositions for diagnostic and chemotherapeutic purposes.

The α-D-arabinofuranosyl nucleosides and nucleotides of the present invention are represented by Formula Ia:

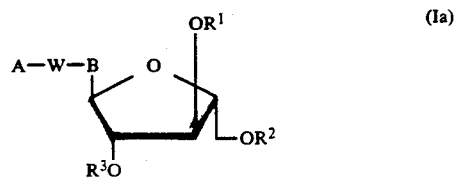
(Ia)

The oligomers of the present invention are represented by Formula Ib below:

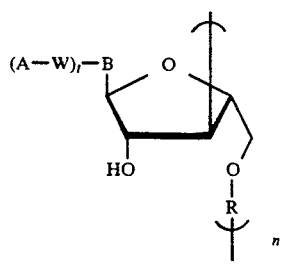
(Ib)

The symbols in these formulas are defined as follows:

B is a nucleotide base and, in the case of the oligomers of Formula Ib, will either be the same base in all units of the oligomer or will vary from one unit to the next;

$R^1$ is either hydrogen or a reactive group suitable for internucleotide bond formation;

$R^2$ is either hydrogen or a protecting group;

$R^3$ is either hydrogen or a protecting group;

R is phosphate, phosphorothioate, phosphoramidate, or alkanephosphonate, and either is the same in all units of the oligomer or varies from one unit to the next, and is preferably monophosphate;

t is zero or one, and either is the same in all units of the oligomer or varies from one unit to the next, with the proviso that t is 1 on at least one of the units, including oligonucleotides in which t is zero on at least one of the units as well as oligonucleotides in which t is 1 on all of the units;

W is a chemical linker arm;

A is an intercalator, a crosslinking agent, a group capable of binding double-stranded DNA, a reporter group, or a group capable of binding one or more reporter groups; and n is an integer greater than 1, representing the number of units in the oligomer, and is preferably 5 to 2000, most preferably 10 to 100.

Preferred examples of reactive groups suitable for internucleotide bond formation are phosphorus-containing groups such as phosphate, diphosphate, triphosphate, phosphorothioate, alkyl phosphochloridites, alkyl phosphoramidites, alkanephosphonates, and activated phosphate diesters. Examples of protecting groups are trityl, methoxytrityl, dimethoxytrityl, 9-phenylxanthen-9-yl, benzoyl, isobutyryl and acetyl. Examples of other groups listed in these definitions are given below.

Included in the invention is the discovery that the monomer units exhibit a highly selective capping reaction at the 2'-position of the α-D-arabinofuranosyl ring when both the 2'- and 3'-positions are exposed, facilitating the appropriate derivatization of the units for use in oligonucleotide synthesis.

The oligonucleotides are useful in the identification, isolation, localization and/or detection of complementary nucleic acid sequences of interest in cell-free or cellular systems. Therefore, the invention further provides a method for identifying target nucleic acid sequences, which method comprises utilizing an oligonucleotide probe comprising at least one of a labeled α-arabinofuransoyl nucleotide moiety.

The oligonucleotides of the invention are also useful as chemotherapeutic agents to control the expression of gene sequences or to inhibit mRNA translation.

DETAILED DESCRIPTION OF THE INVENTION

The monomer units and oligomers of the present invention contain α-D-arabinofuranosyl structures in place of the naturally-occurring α-D-ribo- or 2'-deoxy-α-D-ribonucleosides found in RNA and DNA, respectively. They also contain the o-linkage between the sugar and the heterocyclic base of the nucleoside, which confers nuclease resistance and tight complementary strand binding to the oligonucleotides.

Suitable nucleotide bases as represented by B in Formulas Ia and Ib are those which are susceptible to hybridization. These nucleotide bases may thus be the purines, the pyrimidines, and analogs of purines and pyrimidines such as 3- and 7-deazapurines and pyrazolo{3,4-d}pyrimidines. Other nucleotide bases may also be used, however. In particular, any base compatible for hybridizing with DNA or RNA may be used. Examples of nucleotide bases meeting this description are adenin-9-yl, guanin-9-yl, 7-substituted-7-deazaadenin-9-yl, 7-substituted-7-deazaguanin-9-yl, 8-substituted-adenin-9-yl, 8-substituted-guanin-9-yl, thymin-1-yl, uracil-1-yl, cytosin-1-yl, 5-substituted-uracil-1-yl, 5-substituted-cytosin-1-yl, 3-substituted-4-amino-pyrazolo{3,4-d}pyrimidin-1-yl, and 3-substituted-6-amino-4-oxo-pyrazolo(3,4-d}pyrimidin-1-yl. Preferred bases are adenine, guanine, thymine, cytosine and uracil.

As indicated above, the definition of $R^1$ in Formula Ia includes reactive groups suitable for internucleotide bond formation. These reactive groups are groups which are useful during chain extension in the synthesis of an oligonucleotide. Reactive groups which are particularly useful in this regard are phosphorus-containing groups. Examples are alkyl phosphochloridites, alkyl phosphoramidites, and activated phosphate diesters.

The definitions of $R^2$ and $R^3$ include protecting groups, which are groups which block the oxygen to which they are attached from reactions other than those used to remove these groups. Examples are given below.

The functional group A in Formulas Ia and Ib is defined to include intercalators, crosslinking agents, reporter groups, groups capable of binding one or more reporter groups and groups capable of binding double-stranded DNA.

Intercalators are planar aromatic bi-, tri- or polycyclic molecules whose dimensions are roughly the same as those of a purine-pyrimidine pair and which can insert themselves between two adjacent base pairs in a double stranded helix of nucleic acid. Intercalators have been used to cause frameshift mutations in DNA and RNA. It has also been shown that when an intercalator is covalently bound via a linker arm ("tethered") to the end of a deoxyoligonucleotide, the intercalator increases the binding affinity of the oligonucleotide for its target sequence, resulting in strongly enhanced stability of the complementary sequence complex. Some tethered intercalators also protect the oligonucleotide against exonucleases, although not against endonucleases. See Sun, J. S., et al., *Nucleic Acids Res.* 15:6149–6158; and Doan, T. L., et al., *Nucleic Acids Res.* 15:7749–7760. Examples of tetherable intercalating agents are oxazolopyridocarbazole, acridine orange, proflavine, acriflavine and derivatives of proflavine and acridine such as 3-azido-6-(3-bromopropylamino)acridine, 3-amino-6-(3-bromopentylamino)acridine, and 3-methoxy-6-chloro-9-(5-hydroxypentylamino)acridine Functional groups which are crosslinkers serve a variety of functions in the species of the present invention. In chemotherapeutic applications, for example, the oligonucleotides of the present invention may be used to increase the efficiency of inhibition of mRNA translation or gene expression control. The oligonucleotides accomplish this by inducing irreversible damage in a target complementary sequence. This is achieved by crosslinking agents covalently attached to the oligonucleotide, the crosslinking agents capable of inducing chain breaks in the complementary sequence. Breaks in the sequence chain can also be caused by other functional groups as well, notably moieties which are capable of forming complexes of metals that generate hydroxyl radicals.

A variety of crosslinkers may be used. One example of a type of crosslinkages which cause chain breakages are those which do so when exposed to alkaline conditions, such as by treatment with piperidine. Examples include α-halocarbonyl compounds, 2-chloroethylamines and epoxides. These and other examples of crosslinking reagents which perform a similar function are disclosed by Knorre, D. G., et al., *Progress in Nucleic Acid Research and Molecular Biology* 32:291–320 (1985); and Hélène, C., et al., *Molecular Mechanisms of Carcinogenic and Antitumor Activity*, Chagas and Pullman, Eds., Adenine Press, pp. 205–222.

The use of reporter groups, or groups capable of binding one or more reporter groups, as the functional group A occurs when the α-arabinofuranosyl oligonucleotides of the invention serve as probes in nucleic acid assays. These groups are effective in detecting the presence of hybridizable polynucleotides.

Reporter groups are groups which have a physical or chemical characteristic which can be measured or detected. Detectability may be provided by such characteristics as color change, luminescence, fluorescence, or radioactivity; or it may be provided by the ability of the reporter group to serve as a ligand recognition site.

Examples of reporter groups utilizing radioactivity are groups bearing $^3H$, $^{125}I$, $^{34}S$, $^{14}C$, or $^{32}P$ atoms. Further examples of reporter groups are fluorophores, chemiluminescent agents, enzymes or enzyme substrates. Still further types of reporter groups are those which include ligands which bind to antiligands such as antibodies or other species capable for forming a ligand-antiligand complex, the antiligand being either inherently detectable or covalently bound to a label capable of emitting a detectable signal, such as a fluorophore, chemiluminescent agent, enzyme, or the like. Ligands and antiligands may be varied widely. Where a ligand has a natural "antiligand", namely ligands such as biotin, thyroxine, and cortisol, it can be used in conjunction with its labeled, naturally occurring antiligand. Alternatively, any haptenic or antigenic compound can be used in combination with a suitably labeled antibody. A preferred labeling method utilizes biotin-labeled analogs of oligonucleotides, as disclosed in Langer, P., et al., *Proc. Natl. Acad. Sci. USA* 78:6633–6637 (1981), which is incorporated herein by reference. The optimum choice of reporter group for any particular application, and its method of attachment, direct or indirect, will depend on such considerations as the sensitivity required, the ease of conjugation with the probe, stability requirements, and available instrumentation.

Prime examples of enzyme reporter groups are hydrolases, particularly phosphatases, esterases, ureases and glycosidases, or oxidoreductases, particularly peroxidases. Examples of fluorescent compounds are fluorescein and its derivatives, rhodamine and its derivatives, dansyl, and umbelliferone. Examples of chemiluminescers are luciferin and 2,3-dihydrophthalazinediones such as luminol.

Prominent examples of groups capable of binding one or more reporter groups are groups which exhibit nucleophilic properties. Examples of such groups are those containing aliphatic or aromatic amines, carboxylic acids, hydroxyls and the like.

Examples of groups capable of binding double-stranded DNA are antibodies with antibody binding sites specific for double-stranded DNA. These are likewise known in the art and serve a variety of purposes.

The amount of labeled probe present in the hybridization solution may vary widely, depending upon the nature of the label, the amount of the labeled probe that can reasonably bind to the cellular target nucleic acid, and the precise stringency of the hybridization medium and/or wash medium. Generally, substantial probe excesses over the stoichiometric amount of the target will be employed to enhance the rate of binding of the probe to the target nucleic acids.

The chemical linker arm represented by W in Formulas Ia and Ib enhances the ability of the functional group A to interact with any of the various species with which it must interact to perform its function. These species, as indicated above, include antibodies, detector proteins, or chemical reagents. The linker arm holds the functional group at a suitable distance from the base when the base is paired with another in the double stranded formation. Linker arms may include alkylene groups of 1 to 12 carbon atoms, alkenylene groups of 2 to 12 carbon atoms and 1 or 2 olefinic bonds, alkynylene groups of 2 to 12 carbon atoms and 1 or 2 acetylenic bonds, or these groups substituted at a terminal end with a nucleophilic group such as oxy, thio, amino, carbonyl, amido or epoxy. Such functionalities, including aliphatic or aromatic amines, exhibit nucleophilic properties and are capable of serving as a point of attachment of the functional group A. Groups such as malonamido are also contemplated for use as a linker arm in the present invention.

Preferred linker arms contain carbon atom chains at least three carbon atoms in length. The terminal nucleophilic group is preferably amino or amido.

The linker arm is preferably attached to the nucleotide base at the 8-position when B is a purine, the 5-position when B is a pyrimidine, the 3-position when B is a 3-deazapurine, the 7-position when B is a 7-deazapurine, or the 3-position when B is a pyrazolo{3,4-d}-pyrimidine. Thus, in structures using the five common bases, for nucleotides in which B is adenine or guanine and t is one, W is joined at the 8-position of B; for nucleotides in which B is cytosine or uracil and t is one, W is joined at the 5-position of B. Nucleotides in which B is thymine will generally not contain a linker arm, nor likewise a functional group A.

Preferred oligonucleotides of the present invention in accordance with Formula Ib are those in which t is one in at least one monomeric nucleotide unit, and the oligomer further contains monomeric units in which t is zero. Preferred oligonucleotides are those containing from one to twenty units in which t is one, with additional units in which t is zero comprising the remainder.

The species of Formula Ia may be prepared from known starting materials by methods known in the art. In addition, the starting materials themselves may be prepared by methods in the literature. For example, 9-(α-D-arabinofuranosyl)adenine may be synthesized by the method described by Bristow and Lythgoe, *J. Chem. Soc.* 2306-2309 (1949). A preparation of 9-(α-D-arabinofuranosyl)guanine and -isoguanine is described by Lee, W. W., et al., *J. Med. Chem.* 14:819-823 (1971). A preparation of 1-(α-D-arabinofuranosyl)uracil and -thymine is described by Nishimura and Shimizu, *Chem. Pharm. Bull.* 13:803-810 (1965). A preparation of 1-(α-D-arabinofuranosyl)cytosine is described by Montgomery and Thomas, *J. Heterocyclic Chem.* 16:353-357 (1979).

Protecting groups are introduced onto these starting materials by conventional techniques, and the resulting intermediates are activated for use in the synthesis of oligonucleotides. Conversion of the intermediates to protected, activated forms is achieved according to the procedures analogous to those described in detail for 2'-deoxynucleosides in several reviews. See, for example, Sonveaux, *Bioorganic Chemistry* 14:274-325 (1986); Jones, R. A., in *Oligonucleotide Synthesis, a Practical Approach*, M. J. Gait, Ed., IRL Press, p. 23-34 (1984).

One reaction scheme, in which thymine is the base B, is shown below as Scheme 1. Note that the starting nucleoside II is an inverted view of Formula Ia for convenience in showing the reactive portions of the molecule.

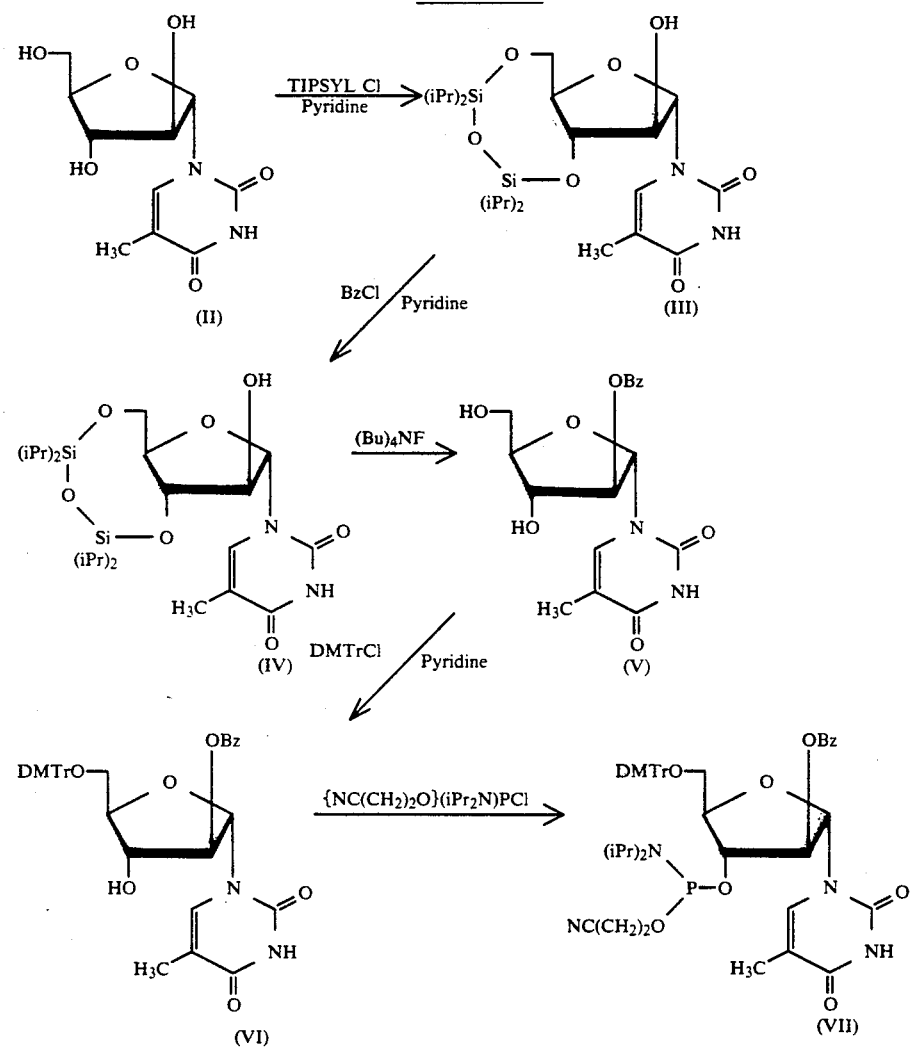

SCHEME 1:

As outlined in Scheme 1, the nucleoside (II) is treated with 1,3-dichloro-1,1,3,3-tetraisopropyldisiloxane (TIPSYL Cl) to give the 3',5'-cyclic disiloxane (III), which is then treated with benzoyl chloride (BzCl) to give the 2'-O-benzoate (IV). Treatment with fluoride ion gives the desilylated compound (V), and tritylation of the 5'-OH gives the 2',5'-protected nucleoside (VI). When B is adenine or cytosine, the nucleosides require protection as well at the amine on the base; therefore, such nucleosides are further benzoylated. Guanine requires an isobutyryl protecting group; thus, when B is guanine, the benzoyl derivative is reacted with isobutyryl chloride. In the final step shown in Scheme 1, phosphitylation of the 3'-OH gives the reagent (VII), ready for direct use on an automated DNA synthesizer.

The novel reaction which forms one aspect of the present invention permits one to obtain the same product by an alternate reaction scheme which does not involve the preparation of a 3',5'-cyclic disiloxane intermediate and thereby eliminates two steps. This novel reaction is a capping reaction of an α-D-arabinofuranosyl nucleotide with exposed hydroxyls at the 2'- and 3'-positions, and the reaction is discovered to occur selectively at the 2'-position. A nucleotide of the formula

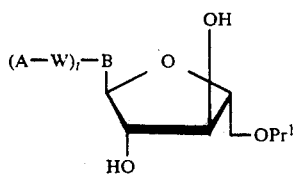

in which:
B is a nucleotide base;
W is a linking group;
A is a member selected from the group consisting of intercalators, crosslinking agents, groups capable of binding double-stranded DNA, reporter groups, and groups capable of binding one or more reporter groups;
t is zero or 1; and
$Pr^1$ is a protecting group;
is reacted with a capping agent which is a $Pr^2$-containing compound capable of bonding the $Pr^2$ group, which is also a protecting group, to a hydroxyl oxygen atom, with the result that the following product is selectively formed:

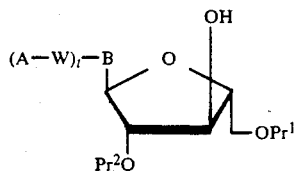

The terms "capping" and "protecting" are used interchangeably in this specification, and are intended to include permanent attachment of species and attachment of species which can be readily removed by subsequent treatment, in accordance with methods well known among those skilled in the art. The capping or protecting groups are any atoms or groups which serve to block the hydroxyl oxygen so protected from other reactions. Thus, for example, capping at the 2'-position serves to restrict such reactions as phosphitylation and chain extension in the formation of oligonucleotides to the unprotected hydroxyl at the 3'-position.

A variety of protecting groups and reactive agents containing them in a form suitable for attachment to a hydroxyl oxygen are known. Examples of particular interest for this invention, for both the above formula and Formula Ia (in which the protecting groups are included in the definition of $R^2$ and $R^3$), are trityl, methoxytrityl, dimethoxytrityl, 9-phenylxanthen-9-yl, benzoyl, isobutyryl, and acetyl. Preferred protecting groups for $Pr^1$ are trityl, methoxytrityl (most notably 4-methoxytrityl), dimethoxytrityl (most notably 4,4'-dimethoxytrityl), 9-phenylxanthen-9-yl, benzoyl, and isobutyryl; and preferred groups for $Pr^2$ are benzoyl and isobutyryl. Most preferred for $Pr^1$ are 4,4'-dimethoxytrityl and 9-phenylxanthen-9-yl, and most preferred for $Pr^2$ are benzoyl and isobutyryl.

The most convenient and widely used reactive precursors for these groups are acyl halides, preferably chlorides, for all groups other than acetyl, and acetic anhydride for the acetyl group. The reactions may be conducted under conditions and procedures well known for capping reactions among those skilled in the art. Approximately equimolar amounts of the nucleoside and the capping reagent are contacted under reactive conditions, generally in liquid solution. A variety of inert organic solvents may be used, a notable example being dry pyridine. For the acetyl protecting group, the reaction is generally conducted in the presence of 4-dimethylaminopyridine which serves as a catalyst, with tetrahydrofuran as a solvent. Pressure and temperature are not critical for these reactions, and may be varied. Atmospheric conditions of temperature and pressure will generally suffice, however. The reactions are quenched, solvents removed, and the products purified by conventional techniques.

An illustration of a reaction scheme which includes this reaction is shown below as Scheme 2. Here again, for purposes of illustration, the base is thymine, and again, the starting nucleoside II is an inverted view of Formula Ia.

SCHEME 2:

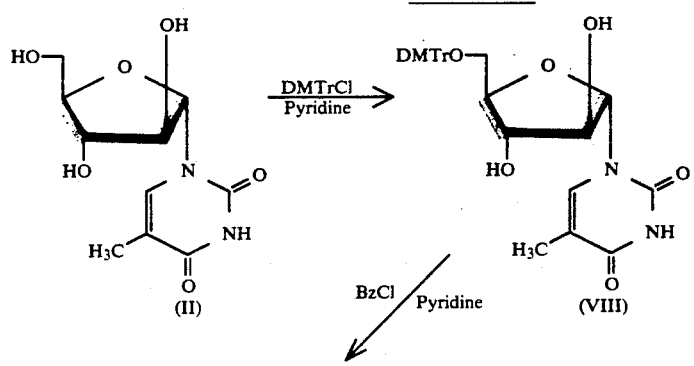

SCHEME 2:
-continued

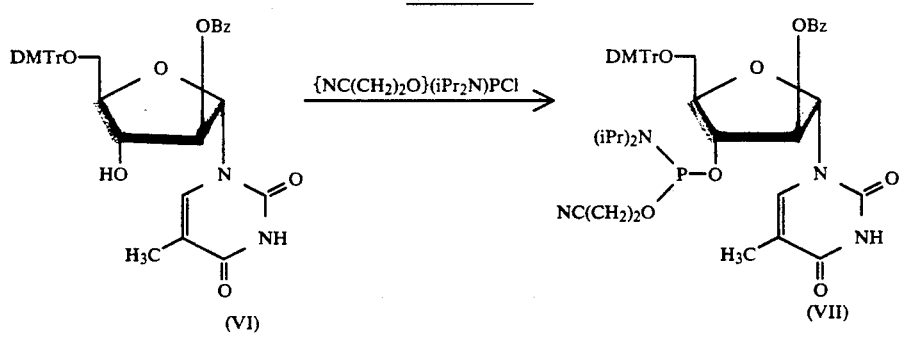

In Scheme 2, the nucleoside (II) is tritylated directly, which occurs selectively, as expected, at the 5'-position. This results in an intermediate with two OH groups, one at the 2'-position and the other at the 3'-position (VIII). When benzoylation is then performed, the reaction proceeds with unexpected selectivity at the 2'-position, rather than producing a mixture of 2'- and 3'-benzoylated species, to give the 2',5'-protected nucleoside (VI). This is readily converted to the 3'-phosphitylated reagent (VII) by the same reaction used in Scheme 1.

Compounds of the invention where $R^1$ or $R^2$ is a mono-, di- or triphosphate may be prepared by processes known in the art.

Activated nucleotides VII prepared according to either Scheme 1 or Scheme 2 or any other reaction scheme are used to synthesize arabino oligonucleotides in a manner analogous to that used for DNA and RNA nucleotides. Nucleotides will be linked in the preselected sequence to form a nucleotide chain which is complementary to a sequence of nucleotides in target DNA or RNA. In a preferred embodiment, the activated nucleotides VII may be used directly on an automated DNA synthesizer according to the procedures and instructions of the particular synthesizer employed. The oligonucleotides may be prepared on the synthesizer using the standard commercial phosphoramidite (described in Gait, M. J., in *Oligonucleotide Synthesis, A Practical Approach,* supra) or H-phosphonate chemistries. In such preparation, the nucleoside to be used at the 3'-end of the desired sequence is treated with succinic anhydride and coupled to a standard commercial CPG bead using the method of Atkinson, T., et al., in *Oligonucleotide Synthesis, A Practical Approach,* supra.

The oligonucleotides may conveniently be purified by reverse-phase HPLC.

The oligonucleotides of the present invention bind in a parallel sense to complementary strands. When sequences are designed to be antisense to target mRNA or DNA for chemotherapeutic use, for example, they are coded with the 3'-end of the desired oligonucleotide corresponding to the 3'-end of the target sequence.

Target nucleic acid sequences may be identified in accordance with the invention by the use of an oligonucleotide probe comprising at least one labeled α-arabinofuranosyl nucleotide moiety as described above. A typical procedure is as follows:

(a) Nucleic acids in the sample to be tested are first denatured.

(b) A labeled α-arabinofuranosyl oligonucleotide probe is then hybridized to the target nucleic acids, the probe including a sequence complementary to that of the target nucleic acids.

(c) The sample is then washed to remove unbound probe.

(d) The sample is then incubated with detection agents.

(e) Finally, the sample is inspected for signals indicating hybridization by the probe.

Each of these steps may be conducted by procedures well known in the art. Hybridization techniques, for example, include homogenous hybridizations where both complementary nucleic acids are free in solution, and heterogeneous hybridizations where one nucleic acid is bound to a solid support such as a slot blot or a support as used in a Southern transfer assay. Examples of hybridization methods which can be used are described in *Nucleic Acid Hybridization, A Practical Approach,* Hames, B. D. and Higgins, S. J., Eds., IRL Press (1985).

Kits for performing assays of this type will typically contain the following components:

a probe reagent component comprising a labeled α-arabinofuranosyl oligonucleotide having a sequence complementary to that of the target nucleic acids;

a denaturation reagent for converting double stranded nucleic acid to single stranded nucleic acid; and Where appropriate, such kits will also include a signal-generating system, such as for example an enzyme and an enzyme substrate.

The following examples are provided for purposes of illustration, and are intended neither to limit nor define the present invention in any manner.

Examples 1 through 3 illustrate Scheme 1 up to Compound VI, with thymine as the base as shown in the equations.

EXAMPLE 1

1-(3',5'-O-Tetraisopropyldisiloxan-1",3"-yl-α-D-arabinofuranosyl)thymine (Compound III)

To a solution of 1-α-D-arabinofuranosylthymine (Compound II) (300 mg, 0.85 mmol) in dry pyridine (15 mL) was added 1,3-dichloro-1,1,3,3-tetraisopropyldisiloxane (0.38 mL, 0.85 mmol). The resulting solution was stirred 18 h. Pyridine was then evaporated from the solution and the residue was partitioned between ethyl acetate and water. The organic phase was washed with cold 1N HCl, $H_2O$, saturated aqueous $NaHCO_3$, and aqueous NaCl, then dried over $Na_2SO_4$. Flash chromatography using 5% acetone/methylene chloride gave 230 mg (54%), m.p. 80°–96° C., identified as Compound III by the following:

H NMR (CDCl$_3$): 9.1 (1H, br s, NH), 7.35 (1H, s, H-6), 5.55 (1H, d, H-1', J=4.8), 4.5–3.8 (6H, m, other sugar protons), 1.95 (3H, s, CH$_3$), 1.2–0.9 (26H, m, i-Pr).

Elemental Analysis:

Calculated for C$_{22}$H$_{39}$N$_2$O$_7$Si$_2$: C, 52.88; H, 7.87; N, 5.61;

Found: C, 52.50; H, 7.93; N, 5.37.

EXAMPLE 2

1-(2'-O-Benzoyl-α-D-arabinofuranosyl)thymine (Compound V)

To a cold solution of 1-{3',5'-O-(tetraisopropyldisiloxan-1",3"-diyl)-α-D-arabinofuranosyl}thymine (Compound III) (0.9 g, 1.8 mmol) in dry pyridine (10 mL) was added benzoyl chloride (0.2 mL, 1.8 mmol). After being stirred at ambient temperature 4 h, the mixture was poured into ice/water, then extracted with ethyl acetate. The organic phase was dried and evaporated and the residue (Compound IV) was used without further purification. To this product (Compound IV) (600 mg, 1.2 mmol) was added 10 mL of 1N tetra-n-butylammonium fluoride in tetrahydrofuran, and stirring was continued for 2 h. The solvent was then evaporated, and the residue was purified by flash chromatography on silica gel, using 10% acetone/hexanes. The fractions containing product were collected and evaporated to give 100 mg (12%). The product was identified as Compound V by the following:

H NMR (d$_6$-DMSO): 11.34 (1H, s, NH), 8.1–7.5 (5H, m, ArH), 7.73 (1H, s, H-6), 5.97 (1H, d, H-1', J=4.80), 5.89 (1H, d, 3'-OH, J=4.80), 5.51 (1H, t, H-2', J=4.95), 4.99 (1H, t, 5'-OH, J=5.70), 4.45–4.25 (2H, m, H-3' and H-4'), 3.7–3.5 (2H, m, H-5'), 1.82 (3H, s, CH$_3$).

EXAMPLE 3

1-{2'-O-Benzoyl-5'-(dimethoxytrityl)-α-D-arabinofuranosyl}thymine (Compound VI)

To 1-(2'-O-benzoyl-α-D-arabinofuranosyl)thymine (Compound V) (60 mg, 0.13 mmol) in pyridine (10 mL) was added 4,4'-dimethoxytrityl chloride (80 mg, 0.23 mmol), and the mixture was stirred for 18 h at ambient temperature. Solvents were removed in vacuo and the product was isolated on preparative TLC, with development in 30% acetone/hexanes, giving 30 mg (28% yield) of product. Its identity as Compound VI was confirmed by the following:

H NMR: 8.1–6.7 (19H, m, ArH), 6.02 (1H, d, H-1', J=4.5 Hz), 5.39 (1H, m, H-2'), 4.55 (2H, m, H-3' and H-4'), 3.78 (6H, s, OCH$_3$), 3.67 (2H, m, H-5'), 2.00 (3H, s, CH$_3$).

Elemental Analysis:

Calculated for C$_{38}$H$_{38}$N$_2$O$_9$: C, 68.46; H, 5.74; N, 4.20;

Found: C, 68.25; H, 5.52; N, 4.01.

Examples 4 through 8 illustrate Scheme 2, using thymine again as the base, and including the preparation of the nucleoside starting material and proceeding eventually to Compound VII.

EXAMPLE 4

1-(2',3',5'-Tri-O-benzoyl-α-D-arabinofuranosyl)thymine

A mixture of dry thymine (0.5 g, 3.96 mmol), hexamethyldisilazane (30 mL), ammonium sulfate (50 mg), and dry pyridine (1.0 mL) was refluxed for two hours. The solvents were then removed under vacuum. The resulting residue was added to a solution of 1-O-acetyl-2',3',5'-tri-O-benzoyl-α-D-arabinofuranose (2.0 g, 3.96 mmol) in dry acetonitrile (50 mL). Trimethylsilyl trifluoromethanesulfonate (0.765 mL, 3.96 mmol) was then added and the mixture was stirred for 18 h. Solvents were evaporated and the residue was dissolved in ethyl acetate. This solution was washed with a solution of saturated sodium bicarbonate, then a solution of saturated sodium chloride, and dried over sodium sulfate. Flash chromatography on silica gel using a step gradient of 10% acetone/hexane to 50% acetone/hexanes gave the product, which was dried to give 1.0 g (44.3% yield); m.p. 90° C. Identity of the product was confirmed by the following:

H NMR (CDCl$_3$): 8.83 (1H,s,NH), 8.2–7.4 (15H, m, ArH), 7.30 (1H, s, H-6), 6.29 (1H, d, H-1', J=3.29 Hz), 5.95 (1H, t, J=2.85), 5.77 (1H, t, J=3.0), 4.98 (1H, m, H-4'), 4.73 (2H, m, H-5'), 1.95 (3H, s, CH$_3$).

Elemental Analysis:

Calculated for C$_{31}$H$_{26}$N$_2$O$_9$: C, 65.26; H, 4.59; N, 4.91;

Found: C, 64.87; H, 4.75; N, 4.51.

EXAMPLE 5

1-α-D-Arabinofuranosylthymine (Compound II)

1-(2',3',5'-Tri-O-benzoyl-α-D-arabinofuranosyl)thymine (18.6 g, 32.6 mmol) was dissolved in dry methanol and adjusted to pH 11 (as indicated by moist pH test paper) with freshly prepared sodium methoxide. After being stirred overnight, the solution was treated with Dowex-50 H$^+$ resin, filtered, and evaporated to dryness. The residue was washed with ethyl acetate and dried, giving a crude yield of 8.0 g (69%). This was used without further purification. Its identity as Compound II was established by the following:

UV: lambda max (pH 7), 267 nm.

H NMR: 11.27 (1H,s, NH), 7.60 (1H, s, H-6), 5.72 (1H, d, H-1', J=4.80), 5.64, 5.44, 4.89 (3H, br s, 2',3',5'-OH), 1.90 (3H, s, CH$_3$), and other sugar protons.

EXAMPLE 6

1-(5'-O-Dimethoxytrityl-α-D-arabinofuranosyl)-thymine (Compound VIII)

To 1-α-D-arabinofuranosylthymine (Compound II) (0.5 g, 1.4 mmol) dissolved in dry pyridine (20 mL) was added 4,4'-dimethoxytrityl chloride (0.656 g, 1.9 mmol). The mixture was stirred for 20 h at ambient temperature, then evaporated to dryness. The residue was dissolved in ethyl acetate (100 mL), then poured into a saturated solution of sodium bicarbonate. The organic layer was washed with H$_2$O and dried over anhydrous sodium sulfate, then evaporated to dryness. The residue was purified by flash chromatography on silica gel using a step gradient of ethyl acetate/hexanes (1/1 to 2/1). The major product was collected and dried to give 0.4 g (49% yield), m.p. 80° C. Its identity as Compound VIII was established by the following:

Elemental Analysis:

Calculated for C$_{31}$H$_{32}$N$_2$O$_8$·0.75 H$_2$O: C, 64.8; H, 5.88; N, 4.88;

Found: C, 65.23; H, 6.04; N, 4.45.

EXAMPLE 7

1-(2'-O-Benzoyl-5'-O-dimethoxytrityl-α-D-arabinofuranosyl)thymine (Compound VI)

To a cold solution of 1-(5'-O-Dimethoxytrityl-α-Darabinofuranosyl)thymine (Compound VIII) (330 mg, 0.57 mmol) in dry pyridine (15 mL) was added benzoyl chloride (0.068 mL, 0.58 mmol). The mixture was stirred at ambient temperature for 4 h, then poured into a saturated solution of sodium bicarbonate and extracted with ethyl acetate. The organic phase was washed with saturated sodium chloride solution and dried over sodium sulfate. The solution was evaporated, and the residue was purified by flash chromatography on silica gel using a step gradient of 20% ethyl acetate/hexanes to 60% ethyl acetate/hexanes. The product was then rechromatographed on preparative HPLC using a $C_{18}$ column (80% $CH_3CN/H_2O$) to give 185 mg (51% yield). Its identity was confirmed by the same analyses performed on the compound produced by Example 3, yielding identical results. This confirms the unusually high selectivity of the reaction at the 2'-position despite the availability of the hydroxyl group at the 3'-position.

EXAMPLE 8

1-{2'-O-Benzoyl-5'-O-dimethoxytrityl-α-D-arabinofuranosyl}thymine 3'-O-(2"-cyanoethoxy-N,N-diisopropyl)phosphoramidite (Compound VII)

To a solution of 1-(2'-O-benzoyl-5'-O-dimethoxytrityl-α-D-arabinofuranosyl)thymine (Compound VI) (460 mg, 0.72 mmol), diisopropylethylamine (0.5 mL), and dichloromethane (40 mL) was added 2-cyanoethyl N,N-diisopropylchlorophosphoramidite (0.448 mL, 1.8 mmol) in two portions. The solution was stirred for 2 h. Methanol (0.1 mL) was added, and the resulting solution was poured into a solution of ethyl acetate (100 mL) and triethylamine (10 mL). This solution was washed with 10% aqueous sodium carbonate, then with saturated aqueous sodium chloride. The organic layer was dried over sodium sulfate, filter, and evaporated. The residue was coevaporated with acetonitrile, dissolved in xylenes (10 mL), and poured into hexanes (300 mL). The precipitated solid was filtered and dried to give 260 mg (43% yield), which was used for oligonucleotide synthesis without further purification.

EXAMPLE 9

Pentadeca{(1-α-D-arabinofuranosyl)thymine 3'-phosphate}

This example illustrates the preparation of an oligomer from the nucleotide of Example VII.

Oligomer preparation was performed on a MilliGen 7500 automated DNA synthesizer (MilliGen/Biosearch, division of Millipore Corporation, Burlington, Mass., U.S.A.). Normal cycle times were used for all reagents and washes, with the exception of the phosphoramidite reagent cycle, which was adjusted to five minutes. The synthesis was conducted on a 1 micromole scale, starting with a "3'-amino tail" column from Glen Research Corporation, Herndon, Va., U.S.A. Deprotection and purification of the oligomer were achieved by conventional methods, as described in *Oligonucleotide Synthesis, A Practical Approach*, Gait, M. J., ed., supra. The oligomer had, by virtue of the solid support column, a $HO(CH_2CH(NH_2)CH_2OPO_3(H)$— group at the 3'-position. This group did not interfere with hybridization.

Although the present invention has been described in some detail by way of example for purposes of clarity and understanding, it will be apparent that other arrangements and equivalents are possible and may be employed without departing from the spirit and scope of the invention. Therefore, the description and illustrations should not be construed as limiting the scope of the invention, which is delineated by the appended claims.

What is claimed is:

1. An oligonucleotide comprising a chain of nucleotide units, each said nucleotide unit having the formula

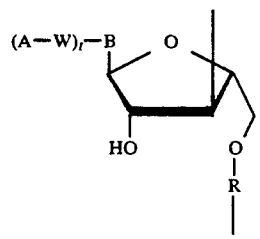

in which:

R is a member selected from the group consisting of phosphate, phosphorothioate, phosphoramidate, and alkanephosphonate, and either is the same in all said nucleotide units or varies among said nucleotide units;

B is a nucleotide base, or a nucleotide base bearing a radioactive atom;

W is an alkylene group having 1 to 12 carbon atoms; an alkenylene group of 2 to 12 carbon atoms and 1 or 2 olefinic bonds; an alkynylene group of 2 to 12 carbon atoms and 1 or 2 acetylenic bonds; —O—, —S—, —NH— —CO—, —NHCO—, —NHCH$_2$CO— or hydroxy-substituted alkylene group having 1 to 12 carbon atoms, —O—, —S—, —NH— —CO—, —NHCO—, —NHCH$_2$CO— or hydroxy-substituted alkenylene group of 2 to 12 carbon atoms and 1 or 2 olefinic bonds, or —O—, —S—, —NH— —CO—, —NHCO—, —NHCH$_2$CO— or hydroxy-substituted alkynylene group of 2 to 12 carbon atoms and 1 or 2 acetylenic bonds, said W forming a linking group between a and B wherein the —O—, —S—, —NH— —CO—, —NHCO—, —NHCH$_2$CO— or hydroxy groups are remote from B;

A is an intercalator, a crosslinking agent, an antibody having a binding site specific for double-stranded DNA, a reporter group, or a biotin residue and A either is the same in all said nucleotide units where t is 1, or varies among said nucleotide units; and t is zero or 1, and either is the same in all said nucleotide units or varies among said nucleotide units.

2. An oligonucleotide in accordance with claim 1 in which t is 1 on at least one of said nucleotide units.

3. An oligonucleotide in accordance with claim 1 in which t is zero on all of said nucleotide units.

4. An oligonucleotide in accordance with claim 1 in which R is monophosphate.

5. An oligonucleotide in accordance with claim 1 in which W includes an aliphatic chain of at least three carbon atoms in length.

6. An oligonucleotide in accordance with claim 1 in which W is an aliphatic chain of at least three carbon atoms in length, terminating with a nucleophilic group at the end adjacent to A.

7. An oligonucleotide in accordance with claim 1 in which W is an aliphatic chain of at least three carbon atoms in length, terminating with an amino or an amido group at the end adjacent to A.

8. An oligonucleotide in accordance with claim 1..in which B is a member selected from the group consisting of purines, pyrimidines, 3-deazapurines, 7-deazapurines, and pyrazolo{3,4-d}pyrimidines.

9. An oligonucleotide in accordance with claim 1 in which B is a member selected from the group consisting of adenine, guanine, thymine, cytosine and uracil.

10. An oligonucleotide in accordance with claim 1 in which B is a member selected from the group consisting of:
purines, at whose 8-position W is joined in nucleotide units where t is 1,
pyrimidines, at whose 5-position W is joined in nucleotide units where t is 1,
3-deazapurines, at whose 3-position W is joined in nucleotide units where t is 1,
7-deazapurines, at whose 7-position W is joined in nucleotide units where t is 1, and
pyrazolo{3,4-d}pyrimidines, at whose 3-position W is joined in nucleotide units where t is 1.

11. An oligonucleotide in accordance with claim 1 in which B is a member selected from the group consisting of:
adenine, at whose 8-position W is joined in nucleotide units where t is 1;
guanine, at whose 8-position W is joined in nucleotide units where t is 1;
thymine, and t is zero in all nucleotide units where B is thymine;
cytosine, at whose 5-position W is joined in nucleotide units where t is 1; and
uracil, at whose 5-position W is joined in nucleotide units where t is 1.

12. An oligonucleotide in accordance with claim 1 in which the number of nucleotide units in said chain is from about 5 to about 2000.

13. An oligonucleotide in accordance with claim 1 in which the number of nucleotide units in said chain is from about 10 to about 100.

14. An oligonucleotide in accordance with claim 1 in which A is a member selected from the group consisting of intercalators, signal-producing reporter groups, and ligands capable of binding to signal-producing antiligands.

* * * * *

UNITED STATES PATENT AND TRADEMARK OFFICE
CERTIFICATE OF CORRECTION

PATENT NO. : 5,177,196
DATED : January 5, 1993
INVENTOR(S) : Rich B Meyer, Jr. et al.

It is certified that error appears in the above-identified patent and that said Letters Patent is hereby corrected as shown below:

Title page [73] "Microprobe" should be —MicroProbe—.

Column 4, line 7, "α-D" should be —β-D—;

Column 4, line 8, "o-linkage" should be —α-linkage—;

Column 4, line 68, after "acridine" add —.—;

Scheme 1, (IV), "OH" should be —OBz—;

Column 12, line 43, after "and" insert a new line —a hybridization reaction mixture—;

column 14, line 25, after ")" add — - —;

Column 14, line 67, after "D" insert — - —;

Column 16, line 43, "a" should be —A—;

Column 17, line 3, after "claim 1" delete "...".

Signed and Sealed this

Twentieth Day of September, 1994

Attest:

Attesting Officer

BRUCE LEHMAN
Commissioner of Patents and Trademarks